United States Patent [19]
Lee et al.

[11] Patent Number: 6,005,157
[45] Date of Patent: Dec. 21, 1999

[54] CYCLOPARAFFIN PURIFICATION FROM PETROLEUM STREAMS

[75] Inventors: Fu-Ming Lee, Katy, Tex.; Randa Wright Wytcherley, Belgrade, Mo.

[73] Assignee: HFM International, Inc., Houston, Tex.

[21] Appl. No.: 09/075,903

[22] Filed: May 11, 1998

[51] Int. Cl.$^6$ .............................. C10G 7/00; C10G 7/10; C10G 7/17

[52] U.S. Cl. .......................... 585/833; 585/826; 585/860; 585/864; 585/865; 585/867; 585/857; 208/313

[58] Field of Search .................................... 585/833, 860, 585/826, 857, 864, 865, 867, 313; 208/313

[56] References Cited

U.S. PATENT DOCUMENTS

| | | | |
|---|---|---|---|
| 2,508,723 | 5/1950 | Mayland et al. | 260/666 |
| 2,771,494 | 11/1956 | Weedman | 260/666 |
| 2,846,485 | 8/1958 | Meason et al. | 260/666 |
| 2,891,894 | 6/1959 | Cier et al. | 202/39.5 |
| 3,034,969 | 5/1962 | Makin, Jr. | 202/39.5 |
| 3,114,783 | 12/1963 | Butler et al. | 260/674 |
| 3,899,412 | 8/1975 | Rowe et al. | 208/92 |
| 4,053,369 | 10/1977 | Cines | 203/52 |
| 4,170,547 | 10/1979 | Atlani et al. | 208/326 |
| 4,921,581 | 5/1990 | Lee et al. | 203/56 |
| 4,944,849 | 7/1990 | Lee | 203/55 |
| 4,948,470 | 8/1990 | Lee | 203/51 |
| 4,948,472 | 8/1990 | Lee et al. | 203/55 |
| 4,954,224 | 9/1990 | Brown et al. | 203/51 |
| 4,955,468 | 9/1990 | Lee | 203/53 |
| 5,032,232 | 7/1991 | Lee et al. | 203/51 |
| 5,055,162 | 10/1991 | Brown et al. | 203/56 |
| 5,069,756 | 12/1991 | Berg | 203/51 |

OTHER PUBLICATIONS

Atkins, G.T. and Boyer, C.M., "Application of McCabe–Thiele Method to Extractive Distillation Calculations," Sep. 1949, Chem. Eng. Prog., vol. 45, No. 9, pp. 553–562.

Chambers, J.M., "Extractive Distillation, Design and Application," Nov. 1951, Chem. Eng. Prog., vol. 47, No. 11, pp. 555–565.

Hachmuth, K.H., "Industrial Viewpoints on Separation Processes," Dec. 1952, Chem. Eng. Prog., vol. 48, No. 12, pp. 617–626.

"Enhanced Distillation," Perry's Chemical Engineers' Handbook, 6$^{th}$ Edition, McGraw–Hill Book Company, 1984, pp. 13–75–13–81.

Primary Examiner—Walter D. Griffin
Assistant Examiner—Tam M. Nguyen
Attorney, Agent, or Firm—Jenkens & Gilchrist, P.C.

[57] ABSTRACT

Disclosed is a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of certain pyrrolidones, certain morpholines, sulfoxides, sulfolanes, glycol compounds, or mixtures thereof, and optionally water; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

47 Claims, 1 Drawing Sheet

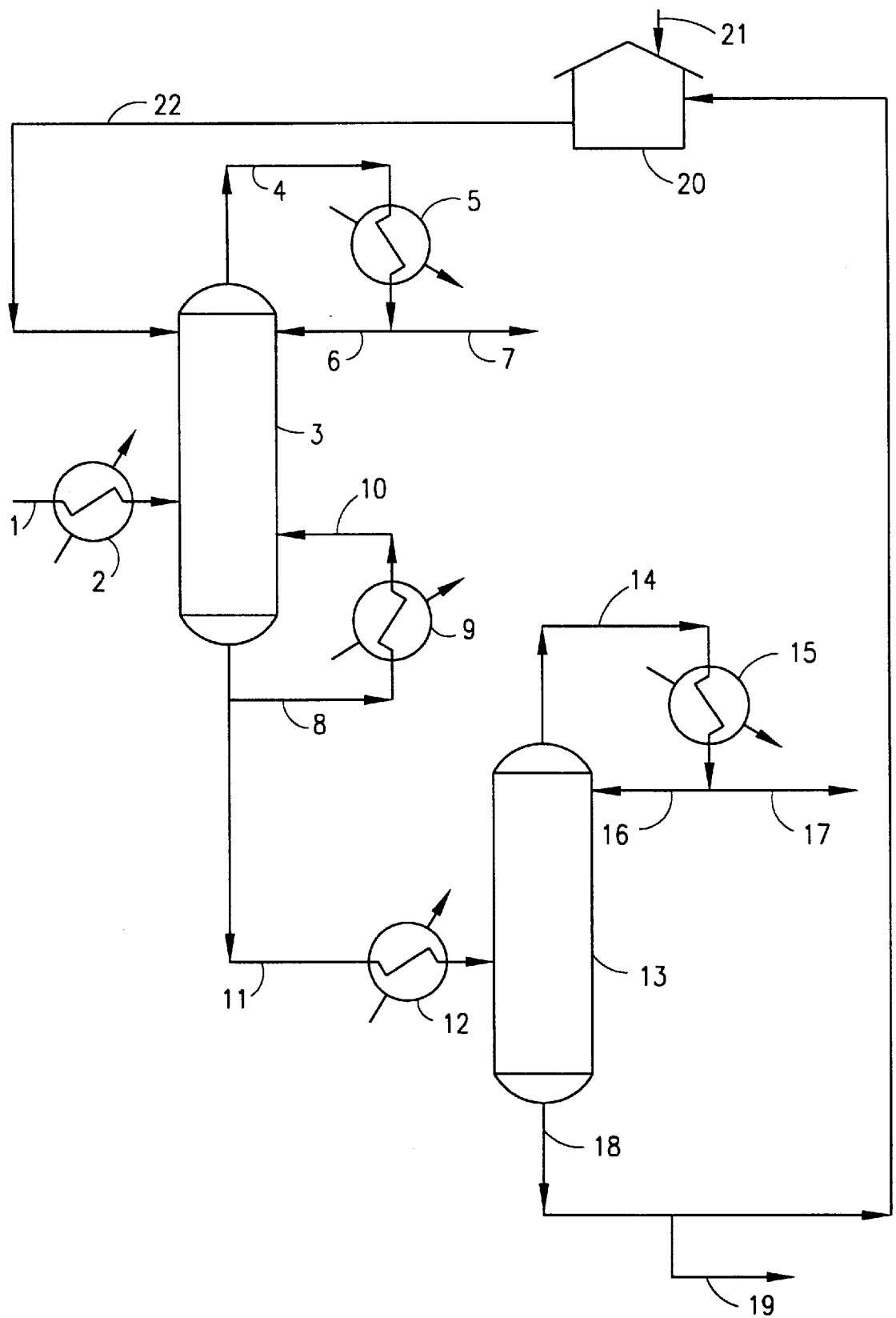

CYCLOPARAFFIN PURIFICATION FROM PETROLEUM STREAMS

This invention relates to processes for separation of very close boiling components in petroleum streams by extractive distillation techniques using certain solvents to raise their relative volatility.

BACKGROUND OF THE INVENTION

Separation of very close boiling components in petroleum streams such as cycloalkanes and alkanes by conventional distillation is both impractical and uneconomical. More specific examples of difficult separations are the separation of cyclohexane and 2,4 dimethylpentane, or cyclopentane and 2,2 dimethylbutane. One of the alternative methods of separating close boiling components is extractive distillation (ED). In an ED column, a polar nonvolatile solvent is introduced into the column near the top to preferentially associate with the more polar components in the feed mixture, so that the relative volatility between the close boiling components can be significantly increased, making the separation possible. The basic principles, design, and operation of ED processes have been thoroughly discussed in the literature: Atkins, G. T. and C. M. Boyer, Chem. Eng. Prog., 45, 553 (1949); Chambers, J. M., Chem. Eng. Prog., 47, 555 (1951); Hackmuth, K. H., Chem. Eng. Prog., 48, 617 (1952); Butler, R. M. and J. A. Bichard, U.S. Pat. No. 3,114,783 (1963); and Perry's Chemical Engineers' Handbook, $6^{th}$ Edition, McGraw-Hill Book Company, 1984, pp. 13–53 to 13–57, the disclosures of which are herein incorporated by reference.

The separation of cycloalkanes (cycloparaffins), in particular cyclohexane or cyclopentane, from close-boiling alkanes (isoparaffins) by extractive distillation is known and has been described in the patent literature, such as in U.S. Pat. Nos. 2,508,723; 2,771,494; 2,846,485; 2,891,894; 3,034,969; 4,053,369; 4,921,581; 4,944,849; 4,948,470; 4,948,472; 4,954,224; 4,955,468; 5,032,232; 5,055,162; and 5,069,756, the disclosures of which are herein incorporated by reference. Some significant improvements have been made recently in formulating mixed solvents in order to effectively separate cycloalkanes from alkanes, in particular cyclohexane or cyclopentane from close-boiling isoparaffins. However, it is highly desirable to develop further improved extractive distillation processes for producing cyclohexane or cyclopentane of high purity from mixtures of isoparaffins, employing single extractive solvents as well as more selective mixed solvents.

SUMMARY OF THE INVENTION

It is an object of this invention to provide an effective process for separating mixtures of close-boiling naphthenes (cycloalkanes) and paraffins (alkanes) by extractive distillation using a polar organic solvent or a mixture of polar organic solvents. It is another object of this invention to produce cyclohexane or cyclopentane of high purity from a mixture comprising cyclohexane or cyclopentane and corresponding close-boiling isoparaffins (i.e., isoparaffins having nearly the same volatility as cyclohexane or cyclopentane) by extractive distillation employing a polar organic solvent or a mixture of polar organic solvents. It is a further object of this invention to provide novel polar organic solvents or novel mixtures of polar organic solvents. Other objects and advantages will be apparent from the detailed description of the invention which follows and the appended claims.

In accordance with this invention, a process is provided for separating at least one cycloalkane (naphthene) containing 5–10 carbon atoms per molecule from at least one close-boiling alkane (paraffin), i.e., one or a plurality of alkanes having nearly the same boiling point at atmospheric pressure conditions as said cycloalkane, by extractive distillation of a feed comprising a mixture of said materials. The improvement includes using as an extractive distillation solvent one of the pyrrolidones (preferably, 2-pyrrolidone), or one of the morpholines (preferably, N-formyl morpholine), or one of the sulfoxides (preferably, dimethyl sulfoxide), or one of the sulfolanes (preferably, unsubstituted sulfolane), or one of the glycols (preferably, tetraethylene glycol), or a mixture of pyrrolidones and morpholines (preferably 2-pyrrolidone and N-formyl morpholine), or a mixture of sulfoxides and glycols (preferably dimethyl sulfoxide and tetraethylene glycol), or a mixture of pyrrolidones and sulfolanes (preferably 2-pyrrolidone and unsubstituted sulfolane).

In a preferred embodiment, the feed cycloalkane is cyclohexane or cyclopentane. In another embodiment, the solvent also comprises 0.1 to 20 weight % water.

BRIEF DESCRIPTION OF THE DRAWING

The drawing is a diagrammatic flow sheet that illustrates the extractive distillation process of the invention.

DETAILED DESCRIPTION OF THE INVENTION

In accordance with the invention, an extractive agent (or solvent) is added to a feed mixture of components to be separated in an extractive distillation (ED) process so that the volatility difference between the components of the mixture is enhanced to the point that an effective separation by distillation becomes possible. The extractive agent and less volatile components flow to the bottom of the distillation column, where the extracted component is withdrawn and recovered by a second or subsequent distillation.

The extractive agent is preferably chosen based on its selectivity for enhancing the relative volatility of the components to be separated and its solvency (solubility) in the feed mixture. Selectivity is a term related to the change in relative volatility of the feed components to be separated. The relative volatility ($\alpha$) is defined as $$\alpha=(Y_1/X_1)/(Y_2/X_2) \qquad (1)$$

where $X_1$ and $X_2$ are the mole fraction of components 1 and 2, respectively, in the liquid phase, and $Y_1$ and $Y_2$ are those in the vapor phase. All components are measured on a solvent-free basis. The larger the difference in $\alpha$ of the feed components to be separated, the easier the separation of the components by fractional distillation becomes. Therefore, a solvent of high selectivity is a solvent which causes great differences in $\alpha$ between the components to be separated, and will allow for the separation of components in a feed mixture with fewer distillation stages, a lower amount of reflux and a higher product purity.

Any hydrocarbon feed which contains at least one naphthene (cycloalkane) containing 5 to 9 carbon atoms per molecule and at least one close-boiling alkane (usually containing 5 to 9 carbon atoms per molecule; more preferably branched alkanes) can be used in the process of this invention. Preferably, the boiling point (at about one atmospheric pressure or 1 atm.) of the cycloalkane(s) and alkane(s) to be separated by ED is in the range of from about 25° to 180° C., more preferably from about 35° to 150° C. In general, the boiling points of the cycloalkane(s) and the alkane(s) differ by about 0.1° to 5° C. (preferably about 0.2° to 3° C.), at about 1 atmosphere.

Non-limiting examples of suitable cycloalkanes for processing for purification in accordance with the invention are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cyclooctane, mixtures thereof, and the like. Presently preferred is cyclohexane or cyclopentane.

Non-limiting examples of suitable alkanes for processing for separation in accordance with the invention are n-pentane, n-hexane, 2-methylpentane, 3-methylpentane, n-heptane, 2,2-dimethylpentane, 2,3-dimethylpentane, 2,4-dimethylpentane, 3,3-dimethylpentane, 2-methylhexane, 3-methylhexane, 2,2,3-trimethylbutane, n-octane, 2-methyloctane, n-nonane, mixtures thereof, and the like. Non-limiting examples of pyrrolidones which are suitable as a solvent for this invention are 2-pyrrolidone (presently preferred), N-methyl-2-pyrrolidone, N-ethyl-2-pyrrolidone, N-propyl-2-pyrrolidone and mixtures thereof.

Non-limiting examples of morpholines which are suitable as solvents for use in this invention are N-formyl morpholine (presently preferred), morpholine, N-methyl morpholine, N-ethyl morpholine, N-propyl morpholine, and mixtures thereof.

Non-limiting examples of sulfoxides which are suitable as solvents for use in this invention are dimethyl sulfoxide (presently preferred), diethyl sulfoxide, dipropyl sulfoxide, and mixtures thereof.

Non-limiting examples of sulfolanes which are suitable as solvents for use in this invention are unsubstituted sulfolane (as referred as 2,3,4,5-tetrahydrothiophene-1,1-dioxide) (presently preferred), 2-methylsulfolane, 3-methylsulfolane, 2,3-dimethylsulfolane, 2,4-dimethylsulfolane, 2-ethylsulfolane, 2,3,4,5-tetramethylsulfolane, and the like, and mixtures thereof.

Non-limiting examples of glycols which are suitable as solvents for use in this invention have a general chemical formula of

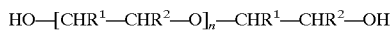

HO—[CHR$^1$—CHR$^2$—O]$_n$—CHR$^1$—CHR$^2$—OH wherein n can be 0, 1, 2, 3, or 4, and R$^1$ and R$^2$ can be independently selected from the group consisting of hydrogen and the methyl group, including ethylene glycol, isopropylene glycol, 1,2-dimethylene glycol, diethylene glycol, diisopropylene glycol, bis(1,2-dimethylene)glycol, triethylene glycol, triisopropylene glycol, tetraethylene glycol (presently preferred), tetraisopropylene glycol, pentaisopropylene glycol, and the like, and mixtures thereof.

Non-limiting examples of mixed solvents which are suitable as solvents for use in this invention are mixtures of pyrrolidones and morpholines (presently preferred being a mixture of 2-pyrrolidone and N-formyl morpholine), mixtures of sulfoxides and glycols (presently preferred being a mixture of dimethyl sulfoxide and tetraethylene glycol), and mixtures of pyrrolidones and sulfolanes (presently preferred being a mixture of 2-pyrrolidone and unsubstituted sulfolane).

Any suitable weight ratio of the solvent to any of the above-described hydrocarbon-containing feed mixtures can be employed. Preferably, the solvent to feed weight ratio is in the range of from about 0.5:1 to 50:1, more preferably from 7:1 to about 20:1.

Any suitable feed entry location to the ED column can be selected for the process of this invention. In general, the feed entry location is in the range of from about 2 to about 70 percent of the total height of the packed or trayed column, measured upward from the bottom of the column, preferably in the range of from about 5 to about 60 percent, more preferably in the range of from 7 to about 60 percent.

Any suitable solvent entry location can be selected for the processes of this invention. Generally, the solvent entry location is in the range of from about 50 to about 99 percent of the total height of the packed or trayed column, preferably in the range of from about 70 to about 99 percent, more preferably in the range of from about 80 to about 99 percent. The solvent entry location should be above the feed entry location to obtain good liquid-liquid contact between feed and solvent.

Any suitable reflux ratio (i.e., the weight ratio of the portion of condensed vapor which is returned to the distillation column to the portion of condensed vapor which is withdrawn as distillate) can be employed in the processes of this invention. In general, the reflux ratio is in the range of from 0.1:1 to about 100:1, preferably in the range of from about 0.5:1 to about 50:1, more preferably in the range of from about 1:1 to about 20:1.

Any suitable temperature in the distillation kettle (reboiler) can be employed in the processes of this invention. The temperature is generally in the range of from about 40° to 210° C., preferably in the range of from about 65° to about 160° C. The ED column is generally heated (more near the bottom, and less near the top). In general, the temperature at the top of the column where the vapor exits into the condenser is in the range of from about 40° to about 150° C., preferably in the range of from about 65° to about 120° C. Solvent and feed are usually preheated (generally to a temperature close to the column temperature of the corresponding entry point) before they are introduced into the packed or trayed column.

Any suitable pressure can be employed during the extractive distillation. The pressure can be from about 0 to about 100 psig, preferably from about 5 to about 20 psig.

The overhead product (withdrawn from the top of the column) contains a smaller volume percent of cycloalkane(s) (preferably cyclohexane or cyclopentane) than the feed and a larger volume percent of alkane(s) (preferably isoalkanes) than the feed. Generally, the bottoms product (withdrawn from the bottom of the column) contains more cycloalkane(s) (preferably cyclohexane or cyclopentane) than the feed, and less of the alkane(s) (preferably isoalkanes) than the feed. Also, the bottoms product contains substantially all of the added solvent, which can be separated from the other bottoms components by simple distillation, since generally the solvent has much higher boiling point than those of the other bottoms components. The recovered lean solvent is then recycled to the ED column.

Any suitable packed length or number of trays in the ED column with suitable column diameter can be employed in the processes of this invention. The exact column dimensions and designs depend on the scale of the operation, the exact feed composition, the exact solvent composition, the desired recovery and degree of purity of the various hydrocarbon products, and the like, can be determined by those having ordinary skill in the art.

The invention can be better understood by reference to FIG. 1 and the following description of a preferred embodiment of the invention. The feed mixture comprising cycloalkane(s) and alkane(s) is introduced through conduit 1 to the middle portion of a multi-stage ED column 3. The temperature of the feed mixture flowing through conduit 1 can be adjusted by controlling heat exchanger 2 so as to add heat to or remove heat from the feed mixture. Solvent from solvent storage 20 is introduced to ED column 3 through conduit 22, and an overhead stream enriched in alkane(s) is withdrawn from the upper portion of ED column 3 through conduit 4. This overhead stream can be completely passed to storage or to other processing units or, as is often the case, the overhead stream can be partially or total condensed, with a portion thereof being returned to ED column 3 as reflux. The overhead stream passing through conduit 4 is condensed in condenser 5 to yield a condensed overhead stream. A portion of the condensed overhead stream can be returned to ED column 3 as reflux through conduit 6, while the remainder of the condensed overhead stream is yielded as product or passed to other processing units through conduit 7.

A bottoms stream is withdrawn from a lower portion of ED column 3 through conduit 11. A portion of the stream withdrawn from the bottom of ED column 3 may be heated and returned to ED column 3. For example, a portion of the bottoms product stream can be withdrawn through conduit 8, heated in reboiler 9 and then passed back to the lower portion of ED column 3 through conduit 10.

Operating conditions in heat exchanger 2, condenser 5 and reboiler 9 can be controlled and interfaced with solvent flow through conduit 22, feed mixture flow through conduit 1, reflux flow through conduit 6 and bottom stream flow through conduit 11 such that the feed mixture introduced into ED column 3 will be fractionated to yield an overhead stream which is enriched in alkane(s) and a bottoms stream predominantly comprising cycloalkane(s) and the solvent.

The bottoms stream passing through conduit 11 can be transferred to storage, used in other processes or, preferably, passed to another distillation column 13 (usually referred as a solvent stripper). Any adjustments to the temperature of the bottoms stream passing through conduit 11 necessary for efficient fractionation (stripping) in column 13 can be made by appropriately adjusting heat exchanger 12. An overhead stream predominantly comprising cycloalkane(s) is withdrawn from the upper portion of column 13 through conduit 14. This overhead stream can be at least partially condensed in condenser 15. A portion of the overhead stream withdrawn from condenser 15 can be returned through conduit 16 as reflux for column 13, with the remainder of the overhead stream being withdrawn as product, i.e., cycloalkane(s) (preferably cyclohexane or cyclopentane) of high purity, through conduit 17.

A bottoms stream predominantly comprising the solvent (usually referred as lean solvent) is withdrawn from the lower portion of column (stripper) 13 through conduit 18. A portion of this bottoms stream is preferably routed back to solvent storage 20 and then recycled to ED column 3, while another portion of the bottoms stream is heated in a reboiler (not shown) and returned to the lower portion of column 13. From time to time impurities which may build up in the solvent can be removed from the system by removing a small purge stream through conduit 19. Solvent lost through the purge stream or through other processing losses may be made up by a makeup stream passing through conduit 21 and into solvent storage 20.

The following examples are presented to further illustrate the invention and are not to be considered as unduly limiting the scope of the invention.

EXAMPLE 1

A typical feedstock for recovering high purity cyclohexane has the following composition:

TABLE I

| Component | Boiling Point (° C.) |
|---|---|
| Cyclohexane | 80.7 |
| 2,2-Dimethylpentane | 79.2 |
| 2,4-Dimethylpentane | 80.5 |
| 2,2,3-Trimethylbutane | 80.9 |
| 3,3-Dimethylpentane | 86.1 |
| 2,3-Dimethylpentane | 89.8 |
| 2-Methylhexane | 90.0 |
| 3-Methylhexane | 92.0 |
| 1,1-Dimethylcyclopentane | 88.2 |

Therefore, in this example, 2,3-dimethylpentane and cyclohexane are chosen as the light key component and heavy key component to be separated, respectively, to demonstrate the effectiveness of 2-pyrrolidone (alone and with 3 weight % water as co-solvent) as an ED solvent for separating cycloalkanes (naphthenes) from alkanes (isoparaffins).

To a hydrocarbon mixture of 86 weight % $CyC_6$ (cyclohexane) and 14 weight % 2,3-DMP (2,3,dimethylpentane) was added an ED solvent of 2-pyrrolidone at a solvent-to-feed ratio (S/F) of 7:1 and 14:1 separately. The total mixture was heated to its boiling point under total reflux conditions for about 20 to 30 minutes in a flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 2,3-DMP and $CyC_6$ in the liquid phase and in the condensed vapor phase were determined by a gas chromatographic method. The relative volatility ($\alpha$) was calculated by Equation (1) (above), where 2,3-DMP is component 1 and $CyC_6$ is component 2. The results are summarized in Table II.

TABLE II

| Added Solvent | S/F | $\alpha$ | Number of Liquid Phases |
|---|---|---|---|
| No solvent added | 0.0 | 0.85 | 1 |
| 2-Pyrrolidone | 7.0 | 1.22 | 1 |
| 2-Pyrrolidone | 14.0 | 1.30 | 1 |
| 2-Pyrrolidone (with 3 wt % $H_2O$) | 14.6 | 1.36 | 1 |

The data in Table II show that, without adding solvent, the relative volatility of 2,3-DMP over $CyC_6$ is 0.85 (less than one) since the boiling point of 2,3-DMP (89.8° C.) is much higher than that of $CyC_6$ (80.7° C). In an ED process, the less polar 2,3-DMP has to be removed as the overhead product and the more polar $CyC_6$ has to be removed as the bottoms product with the solvent, so the relative volatility has to increase to a value larger than 1.0.

As a rule of thumb, the number of theoretical stages of a distillation column is approximately related to the relative volatility by the following equation:

$$N = 4/(\alpha - 1) \tag{2}$$

where N is the number of theoretical stages. As the relative volatility ($\alpha$) approaches to 1.0, N increases substantially and so does the column diameter because of increased reflux ratio. In fact, N can be decreased from 200 to 18, if $\alpha$ is increased from 1.02 to 1.22.

Based on the test results in Table II, it is can be seen that, at S/F of 7.0, 2-pyrrolidone alone is effective to separate 2,3-DMP and $CyC_6$. At S/F of 14.0, the relative volatility increases further from 1.22 to 1.30, showing even better separation between 2,3-DMP and $CyC_6$ by extractive distillation. These results are unexpected because, as is reported conventionally in the literature, a mixed solvent (one component provides selectivity and one component provides solubility) is conventionally required to increase $\alpha$ from 0.85 to 1.22 for separating 2,3-DMP and $CyC_6$.

To lower the melting point of 2-pyrrolidone (24° C.), approximately 3 weight percent of water is added to 2-pyrrolidone. As shown in Table II, with 3 weight percent water in 2-pyrrolidone, the relative volatility of 2,3-DMP over $CyC_6$ increases from 1.30 to 1.36 at about 14:1 solvent-to-feed ratio.

EXAMPLE 2

This example illustrates the effectiveness of another single solvent, N-formyl morpholine in separating 2,3-DMP and $CyC_6$ by extractive distillation. The apparatus and feed described in Example 1 were used for the test series of this example, which was carried out at S/F of 7:1 and 14:1. Test results are summarized in Table III.

TABLE III

| Added Solvent | S/F | α | Number of Liquid Phases |
|---|---|---|---|
| No solvent added | 0.0 | 0.83 | 1 |
| N-formyl morpholine | 7.1 | 1.18 | 1 |
| N-formyl morpholine | 14.2 | 1.27 | 1 |
| N-formyl morpholine (with 3 wt% $H_2O$) | 14.7 | 1.33 | 1 |

Based on the test results in Table III, it can be seen that N-formyl morpholine alone is effective as the extractive solvent for separating 2,3-DMP and $CyC_6$ in an ED process at a solvent-to-feed ratio of 7.0 or higher. Adding 3 weight percent water can further enhance the selectivity of N-formyl morpholine at a solvent-to-feed ratio of 14.7.

EXAMPLE 3

This example illustrates the effectiveness of still another single solvent, dimethyl sulfoxide in separating 2,3-DMP and $CyC_6$ by extractive distillation. The apparatus and feed described in Example 1 were used for the test series of this example, which was carried out at S/F of 7:1 and 14:1. Test results are summarized in Table IV.

TABLE IV

| Added Solvent | S/F | α | Number of Liquid Phases |
|---|---|---|---|
| No solvent added | 0.0 | 0.85 | 1 |
| Dimethyl sulfoxide | 7.0 | 1.20 | 2 |
| Dimethyl sulfoxide | 14.4 | 1.37 | 2 |
| Dimethyl sulfoxide (with 1 wt % $H_2O$) | 14.6 | 1.37 | 2 |
| Dimethyl sulfoxide (with 3 wt % $H_2O$) | 15.0 | 1.47 | 2 |

Based on the test results in Table IV, it can be seen that dimethyl sulfoxide alone is effective as an extractive solvent for separating 2,3-DMP and $CyC_6$ in an ED process at a solvent-to-feed ratio of 7.0 or higher. Adding 1–3 weight percent water to dimethyl sulfoxide can further enhance its selectivity at a solvent-to-feed ratio of 14 to 15.

EXAMPLE 4

This example demonstrates that some solvents, such as sulfolane, tetraethylene glycol, etc., having high selectivity but limited solvency (solubility), tend to have poor performance at low solvent-to-feed ratios, but their performance meets requirements at high solvent-to-feed ratios. The apparatus and feed described in Example 1 were used for the test series of this example, which was carried out at S/F of 7:1 (low solvent-to-feed ratio) and 14:1 (high solvent-to-feed ratio). Test results are summarized in Table V.

TABLE V

| Added Solvent | S/F | α | Number of Liquid Phases |
|---|---|---|---|
| No solvent added | 0.0 | 0.84 | 1 |
| Sulfolane | 7.0 | 1.05 | 2 |
|  | 14.1 | 1.35 | 2 |
| Sulfolane (with 3 wt % $H_2O$) | 14.6 | 1.16 | 2 |
| Tetraethylene Glycol | 7.0 | 1.07 | 2 |
|  | 14.2 | 1.37 | 2 |
| Tetraethylene Glycol |  |  |  |
| (with 1 wt % $H_2O$) | 14.4 | 1.34 | 2 |
| (with 3 wt % $H_2O$) | 14.7 | 1.25 | 2 |

Two liquid phases were observed in all experiments when sulfolane or tetraethylene glycol were used as the ED solvent due to their limited solvency. Two liquid phases tend to reduce the tray efficiency in the ED column, although special tray or packing designs can minimize the problems. Table V clearly shows the poor performance of sulfolane and tetraethylene glycol at low solvent-to-feed ratio (7:1) and good performance at high solvent-to-feed ratio (14:1). Adding water as co-solvent normally improves the solvent selectivity but reduces solvent solvency. Since both sulfolane and tetraethylene glycol have very limited solvency for this application (indicated by two liquid phases), adding water actually decreases the performance for both sulfolane and tetraethylene glycol.

EXAMPLE 5

This example shows that, except in a few cases, a co-solvent does not always help the performance of a single solvent, especially when the particular single solvent has already achieved the required performance for the separation of cycloalkanes and alkanes employing an ED process. The apparatus and feed described in Example 1 were used for the test series of this example, which was carried out at S/F of 7:1 and 14:1. Test results are summarized in Table VI.

TABLE VI

| Added Solvent | S/F | α | Number of Liquid Phases |
|---|---|---|---|
| No solvent added | 0.0 | 0.85 | 1 |
| DMSO/CYCOH (50:50) | 7.0 | 1.12 | 1 |
|  | 14.3 | 1.11 | 1 |
| DMSO/CYCOH (50:50) (with 3 wt % $H_2O$) | 14.9 | 1.10 | 1 |
| DMSO/SULF (50:50) | 7.1 | 1.04 | 2 |
| DMSO/TTEG (50:50) | 6.9 | 1.10 | 2 |
|  | 14.6 | 1.40 | 2 |
| DMSO/NMP (50:50) | 7.2 | 1.15 | 1 |
|  | 14.4 | 1.18 | 1 |
| DMSO/NMP (50:50) (with 3 wt % $H_2O$) | 15.0 | 1.25 | 1 |
| DMSO/MC (50:50) | 7.1 | 1.18 | 1 |
|  | 14.2 | 1.23 | 1 |
| DMSO/MC (50:50) (with 3 wt % $H_2O$) | 14.8 | 1.29 | 1 |
| NFM/NMP (50:50) | 7.0 | 1.11 | 1 |
|  | 14.2 | 1.15 | 1 |

TABLE VI-continued

| Added Solvent | S/F | α | Number of Liquid Phases |
|---|---|---|---|
| NFM/NMP (50:50) (with 3 wt % H₂O) | 14.6 | 1.16 | 1 |
| NFM/MC (50:50) | 7.0 | 1.08 | 1 |
|  | 14.1 | 1.16 | 1 |
| NFM/MC (50:50) (with 3 wt % H₂O) | 14.6 | 1.23 | 1 |
| NFM/CYCOH (50:50) | 7.1 | 1.06 | 1 |
|  | 14.2 | 1.10 | 1 |
| NFM/CYCOH (50:50) (with 3 wt % H₂O) | 14.7 | 1.13 | 1 |
| NFM/2PYRO (50:50) | 7.0 | 1.22 | 1 |
|  | 14.1 | 1.32 | 1 |
| NFM/2PYRO (50:50) (with 3 wt % H₂O) | 14.7 | 1.35 | 1 |
| 2PYRO/DMSO (50:50) | 7.0 | 1.20 | 2 |
|  | 14.2 | 1.34 | 1 |
| 2PYRO/DMSO (50:50) (with 3 wt % H₂O) | 14.7 | 1.41 | 1 |
| 2PYRO/SULF (50:50) | 7.0 | 1.12 | 2 |
|  | 14.1 | 1.37 | 1 |
| 2PYRO/DMSO (50:50) (with 3 wt % H₂O) | 14.7 | 1.34 | 1 |

Based on the data in Table VI, it is observed that, except DMSO/TTEG, NFM/2PYRO, and 2PYRO/SULF at S/F of 14:1, all mixed solvents show lower performance (selectivity) than the component solvents which already achieve the required performance alone. Adding water to the mixed solvents normally improves their performance.

Reasonable variations, modifications and adaptations for various usages and conditions can be made within the scope of the disclosure and the appended claims, without departing from the scope of this invention.

That which is claimed is:

1. In a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of an extractive distillation solvent having an organic component and an optional water component, the organic component of which is selected from the class consisting of N-alkyl morpholine, wherein the alkyl group thereof consists of formyl, methyl, ethyl or propyl, sulfoxides, sulfolanes alone, or glycol compounds alone, and which may optionally contain water; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

2. A process in accordance with claim 1 wherein said at least one cycloalkane is selected from the group consisting of cyclopentane, cyclohexane and mixtures thereof.

3. A process in accordance with claim 1, wherein said at least one cycloalkane is selected from the group consisting of cyclopentane, cyclohexane and mixtures thereof, and said at least one alkane is at least one close-boiling isoalkane.

4. A process in accordance with claim 1, wherein the weight ratio of said solvent to said feed is in the range of from about 0.5:1 to about 50:1.

5. A process in accordance with claim 1, wherein said feed boils at a temperature in the range of from about 25° C. to about 180° C., at a pressure of about 1 atm.

6. A process in accordance with claim 1, wherein the boiling point of said at least one cycloalkane and the boiling point of said at least one alkane differ about 0.1° C. to about 5° C., at a pressure of about 1 atm.

7. In a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of N-alkyl morpholine as the extractive distillation solvent, wherein the alkyl group consists of formyl, methyl, ethyl, and propyl; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

8. A process in accordance with claim 7, wherein said solvent is N-formyl morpholine.

9. A process in accordance with claim 7, wherein said at least one cycloalkane is selected from the group consisting of cyclopentane, cyclohexane and mixtures thereof.

10. A process in accordance with claim 7, wherein said at least one cycloalkane is selected from the group consisting of cyclopentane, cyclohexane and mixtures thereof, and said at least one alkane is at least one close-boiling isoalkane.

11. A process in accordance with claim 7, wherein the weight ratio of said solvent to said feed is in the range of from about 0.5:1 to about 50:1.

12. A process in accordance with claim 7, wherein said feed boils at a temperature in the range of from about 25° C. to about 180° C., at a pressure of about 1 atm.

13. A process in accordance with claim 7, wherein the boiling point of said at least one cycloalkane and the boiling point of said at least one alkane differ about 0.1° C. to about 5° C., at a pressure of about 1 atm.

14. In a process for separating at least one cycloalkane containing 5–10 carbon atoms per molecule from at least one close-boiling alkane by extractive distillation of a feed consisting essentially of said at least one cycloalkane and said at feast one alkane, the improvement comprising the use of sulfoxides as the extractive distillation solvent; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

15. A process in accordance with claim 14, wherein said solvent is dimethyl sulfoxide.

16. A process in accordance with claim 14, wherein said at least one cycloalkane is selected from the group consisting of cyclopentane, cyclohexane and mixtures thereof.

17. A process in accordance with claim 14, wherein said at least one cycloalkane is selected from the groups consisting of cyclopentane, cyclohexane and mixtures thereof, and said at least one alkane is at least one close-boiling isoalkane.

18. A process in accordance with claim 14, wherein the weight ratio of said solvent to said feed is in the range of from about 0.5:1 to about 50:1.

19. A process in accordance with claim 14, wherein said feed boils at a temperature in the range of from about 25° C. to about 180° C., at a pressure of about 1 atm.

20. A process in accordance with claim 14, wherein the boiling point of said at least one cycloalkane and the boiling point of said at least one alkane differ about 0.1° C. to about 5° C., at a pressure of about 1 atm.

21. In a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of sulfolanes selected from the group consisting of 2,3,4,5-tetrahydrothiophene-1,1-dioxide, 2-methylsulfolane, 3-methylsulfolane, 2,4-dimethylsulfolane, 2-ethylsulfolane, and 2,3,4,5-tetramethylsulfolane, alone, as the extractive distillation solvent; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

22. A process in accordance with claim 21, wherein said solvent is sulfolane.

23. A process in accordance with claim 21, wherein said at least one cycloalkane is selected from the group consisting of cyclopentane, cyclohexane and mixtures thereof.

24. A process in accordance with claim 21, wherein said at least one cycloalkane is selected from the group consisting of cyclopentane, cyclohexane and mixtures thereof, and said at least one alkane is at least one close-boiling isoalkane.

25. A process in accordance with claim 21, wherein the weight ratio of said solvent to said feed is in the range of from about 7:1 to about 50:1.

26. A process in accordance with claim 21, wherein said feed boils at a temperature in the range of from about 25° C. to about 180° C., at a pressure of about 1 atm.

27. A process in accordance with claim 21, wherein the boiling point of said at least one cycloalkane and the boiling point of said at least one alkane differ about 0.1° C. to about 5° C., at a pressure of about 1 atm.

28. In a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of glycol compounds alone as the extractive distillation solvents, which have a general chemical formula of

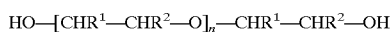
HO—[CHR¹—CHR²—O]ₙ—CHR¹—CHR²—OH where n can be 0, 1, 2, 3, or 4, and $R^1$ and $R^2$ can be independently selected from the group of hydrogen and the methyl group; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

29. A process in accordance with claim 28, wherein said solvent is selected from the group consisting of ethylene glycol, diethylene glycol, triethylene glycol, tetraethylene glycol and pentaethylene glycol.

30. A process in accordance with claim 29, wherein said solvent is tetraethylene glycol.

31. A process in accordance with claim 28, wherein said at least one cycloalkane is selected from the group consisting of cyclopentane, cyclohexane and mixtures thereof.

32. A process in accordance with claim 28, wherein said at least one cycloalkane is selected from the group consisting of cyclopentane, cyclohexane and mixtures thereof, and said at least one alkane is at least one close-boiling isoalkane.

33. A process in accordance with claim 28, wherein the weight ratio of said solvent to said feed is in the range of froth about 7:1 to about 50:1.

34. A process in accordance with claim 28, wherein said feed boils at a temperature in the range of from about 25° C. to about 180° C., at a pressure of about 1 atm.

35. A process in accordance with claim 28, wherein the boiling point of said at least one cycloalkane and the boiling point of said at least one alkane differ about 0.1° C. to about 5° C., at a pressure of about 1 atm.

36. In a process for separating at least one cycloalkane containing 5–10 carbon atoms per molecule from at least one close-boiling alkane by extractive distillation of a feed consisting essentially of said at least one cycloalkane and said at least one alkane, the improvement comprising the use of the mixtures of N-substituted morpholines and pyrrolidones, or the mixtures of sulfoxides and glycols, or the mixtures of mixtures thereof as the extractive distillation solvent; wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

37. A process in accordance with claim 36, wherein said solvent is the mixture of N-formyl morpholine and 2-pyrrolidone, or the mixture of dimethyl sulfoxide and tetraethylene glycol.

38. A process in accordance with claim 36, wherein said at least one cycloalkane is selected from the group consisting of cyclopentane, cyclohexane and mixtures thereof.

39. A process in accordance with claim 36, wherein said at least one cycloalkane is selected from the group consisting of cyclopentane, cyclohexane and mixtures thereof, and said at least one alkane is at least one close-boiling isoalkane.

40. A process in accordance with claim 36, wherein the weight ratio of said solvent to said feed is in the range of from about 7:1 to about 50:1.

41. A process in accordance with claim 36, wherein said feed boils at a temperature in the range of from about 25° C. to about 180° C., at a pressure of about 1 atm.

42. A process in accordance with claim 36, wherein the boiling point of said at least one cycloalkane and the boiling point of said at least one alkane differ about 0.1° C. to about 5° C., at a pressure of about 1 atm.

43. A process in accordance with claim 7, wherein water may optionally be added to the said solvents as a co-solvent to enhance the performance of the said solvents.

44. A process in accordance with claim 14, wherein water may optionally be added to the said solvents as a co-solvent to enhance the performance of the said solvents.

45. A process in accordance with claim 21, wherein water may optionally be added to the said solvents as a co-solvent to enhance the performance of the said solvents.

46. A process in accordance with claim 28, wherein water may optionally be added to the said solvents as a co-solvent to enhance the performance of the said solvents.

47. A process in accordance with claim 36, wherein water may optionally be added to the said solvents as a co-solvent to enhance the performance of the said solvents.

* * * * *